(12) United States Patent
Weaver et al.

(10) Patent No.: US 8,486,895 B2
(45) Date of Patent: Jul. 16, 2013

(54) ANTI-EPIDERMAL GROWTH FACTOR RECEPTOR ANTIBODIES AND USES THEREOF

(75) Inventors: David Weaver, Beijing (CN); Michael Rynkiewicz, Beijing (CN); Cheng Cao, Beijing (CN); Yanwen Jin, Beijing (CN)

(73) Assignee: Guangzhou Yunyuan Biotech Co., Ltd., Guangdong Province (CN)

( * ) Notice: Subject to any disclaimer, the term of this patent is extended or adjusted under 35 U.S.C. 154(b) by 0 days.

(21) Appl. No.: 13/509,237

(22) PCT Filed: Dec. 30, 2009

(86) PCT No.: PCT/CN2009/001603
§ 371 (c)(1),
(2), (4) Date: Aug. 23, 2012

(87) PCT Pub. No.: WO2011/057435
PCT Pub. Date: May 19, 2011

(65) Prior Publication Data
US 2013/0022624 A1    Jan. 24, 2013

(30) Foreign Application Priority Data
Nov. 11, 2009  (CN) .......................... 2009 1 0237803

(51) Int. Cl.
*A61K 39/00*    (2006.01)
*A61K 39/395*    (2006.01)
*A61P 35/00*    (2006.01)
*C07K 16/22*    (2006.01)

(52) U.S. Cl.
USPC ....................................... 514/19.3; 424/133.1

(58) Field of Classification Search
None
See application file for complete search history.

(56) References Cited

U.S. PATENT DOCUMENTS

| 7,598,350 B2 | 10/2009 | Liu et al. |
| 2004/0091485 A1 | 5/2004 | Ellis et al. |
| 2006/0240003 A1 | 10/2006 | Ellis et al. |
| 2007/0264253 A1 | 11/2007 | Liu et al. |
| 2008/0260735 A1 | 10/2008 | Ellis et al. |

FOREIGN PATENT DOCUMENTS

| CN | 1432063 | 7/2003 |
| CN | 101233155 | 7/2008 |

OTHER PUBLICATIONS

International Search Report dated Aug. 12, 2010 issued to international application No. PCT/CN2009/001603.

*Primary Examiner* — Elly-Gerald Stoica
(74) *Attorney, Agent, or Firm* — Knobbe Martens Olson & Bear (57) ABSTRACT

The present invention discloses humanized anti-epidermal growth factor receptor antibodies, which have favorable binding activity (the binding affinity being $5.09 \times 10^{-10}$ mol/L) and are able to inhibit the growth and migration of tumor cells. The present invention also discloses the preparation methods and uses of the antibodies.

19 Claims, 2 Drawing Sheets

ANTI-EPIDERMAL GROWTH FACTOR RECEPTOR ANTIBODIES AND USES THEREOF

CROSS-REFERENCE TO RELATED APPLICATIONS

This application is the U.S. National Phase under 35 U.S.C. §371 of International Application PCT/CN2009/001603, filed Dec. 30, 2009, which was published in a non-English language, which claims priority to CN 200910237803.8, filed Nov. 11, 2009.

FIELD OF THE INVENTION

The present invention relates to an antibody as well as preparation method thereof and uses of the same.

DESCRIPTION OF BACKGROUND

The epidemic growth factor receptor (EGFR) is a member of the family of epidemic growth factor genes (erbB), which is overexpressed in about 30% of human tumors, especially non-small cell lung carcinomas, head and neck squamous cell carcinomas, colorectal carcinomas and the like. Many studies indicate that antibodies against EGFR may effectively inhibit EGFR signal transduction pathway by blocking the binding of ligands extracellularly, which showed promising therapeutic effect on multiple EGFR overexpressing or mutated human tumors, especially head and neck squamous cell carcinomas (80%~100%), colorectal cancer (25%~77%), non-small cell lung cancer (40%~80%) and the like. Epidemic growth factor receptor is one of the current therapeutic targets for tumor that are intensively investigated and well-focused at present. Utilizing genetic engineering in developing an anti-EGFR monoclonal antibody becomes one of research hotspots for immunotherapy of tumor.

In 2004 and 2006, the U.S. Food and Drug Administration had successively approved a murine-human chimeric antibody cetuximab and a full human antibody panitumumab against EGFR for treatment of colorectal carcinomas; in 2005, a humanized antibody nimotuzumab against EGFR was awarded new drug certificate by Chinese State Food and Drug Administration (SFDA), its Phase II/III clinical trial is under way. Use of murine monoclonal antibody in human bodies may induce human anti-murine antibody reaction, and thereby affecting its functions thereof. Application of genetic engineered murine-human chimeric antibody can greatly reduce the immunogenicity of the murine monoclonal antibody, prolong the half life of the antibody in bodies, and further enhance the biological effect of the antibody by virtue of the Fc region of human immunoglobulin mediated immunomodulation and ADCC effect; however, the ability of this chimeric antibody to bind to an antigen is lower than that of the murine antibody by 98.7%. A large number of pre-clinical trials and clinical trials each has proven that cetuximab, alone and in combination with chemotherapy/radiotherapy, has a better therapeutic effect, but simple CDR transplant tends to cause drop in antigen-antibody affinity; panitumumab is a full human antibody prepared with transgenic mice technology, which, comparing with the chimeric antibody and humanized antibody, has a human sequence of near 100%, greatly increasing the antibody-target affinity, but this antibody has such defects as glycosylation pattern of murine, short half life, more hypersensitivity reactions and the like. Nimotuzumab gives a humanized antibody through humanized remodeling of the anti EGFR murine monoclonal antibody, which links the light and heavy chains of the antibody respectively to different expression vectors for expression; since the expressions of the light and heavy chains are quite different, the molecular expression level of the complete antibody tends to be very low.

DISCLOSURE OF THE INVENTION

One of the purposes of the present invention is to provide an antibody that may bind to epidemic growth factor receptor (EGFR).

The present invention provides an antibody, its variable region of heavy chain has an amino acid sequence as set forth by SEQ ID NO. 3 in the sequence listing, and its light chain has an amino acid sequence as set forth by SEQ ID NO. 2 in the sequence listing.

The antibody may be composed of a heavy chain and the light chain, and the heavy chain is composed of the heavy chain variable region and a heavy chain constant region.

The heavy chain constant region has an amino acid sequence as set forth by SEQ ID NO. 11 in the sequence listing.

The encoding gene of the above heavy chain variable region or the encoding gene of the above light chain also belong to the protection scope of the present invention.

Encoding gene of the heavy chain variable region is set forth by the following 1), 2) or 3):

1) a DNA molecule having a nucleotide sequence as set forth by SEQ ID NO. 6 in the sequence listing;

2) a DNA molecule, which hybridizes with the DNA sequence defined in 1) under stringency conditions, and which encodes the heavy chain variable region;

3) a DNA molecule encoding the heavy chain variable region, characterized in that amino acid sequence encoding the heavy chain variable region contains sequence having more than 70% homologous to amino acids at positions 51-70 starting from the N-terminal of SEQ ID NO. 3 in the sequence listing (i.e., nucleotides at positions 153 bp-210 bp starting from the 5' end of SEQ ID NO. 6 in the sequence listing);

Encoding gene of the light chain is set forth by the following I), II) or III):

I) a DNA molecule having a nucleotide sequence as set forth by SEQ ID NO. 5 in the sequence listing;

II) a DNA molecule, which hybridizes with the DNA sequence defined in I) under stringency conditions, and which encodes the light chain;

III) a DNA molecule encoding the light chain, characterized in that amino acid sequence encoding the light chain contains sequence having more than 70% homologous to amino acids at positions 24-34 starting from the N-terminal of SEQ ID NO. 2 in the sequence listing (i.e., nucleotides at positions 72 bp-102 bp starting from the 5' end of SEQ ID NO. 5 in the sequence listing);

Encoding gene of the heavy chain constant region is set forth by the following a) or b):

a) a DNA molecule having a nucleotide sequence as set forth by SEQ ID NO. 12 in the sequence listing;

b) a DNA molecule having a nucleotide sequence as set forth by SEQ ID NO. 13 in the sequence listing.

A primer pair used for amplifying full-length of any of the above encoding genes or any fragment thereof also belongs to the protection scope of the present invention.

The primer pairs are the following primer pairs: the following primer pairs are used for amplifying the light chain encoding genes.

1) one primer sequence is set forth by SEQ ID NO. 7 in the sequence listing, and the other primer sequence of the primer pair is set forth by SEQ ID NO. 8 in the sequence listing;

2) one primer sequence is set forth by SEQ ID NO. 9 in the sequence listing, and the other primer sequence of the primer pair is set forth by SEQ ID NO. 10 in the sequence listing.

A recombinant vector, a recombinant strain, a transgenic cell line or an expression cassette containing any of the above encoding genes also belongs to the protection scope of the present invention.

Another purpose of the present invention is to provide a method for preparing the above antibody.

The method for preparing the above antibody provided by the present invention comprising introducing any of the above encoding genes into a host cell and cultivating to give said antibody.

In the method, any of the above encoding genes may be introduced into the host cell via a recombinant vector; the recombinant vector contains both any of the above encoding genes of the heavy chain variable region and any of the above encoding genes of the light chain, and the encoding gene of the heavy chain variable region and the encoding gene of the light chain are regulated by the same promoter in the recombinant vector.

Another purpose of the present invention is to provide an inhibitor for inhibiting the signal transduction pathway of the epidemic growth factor receptor, an inhibitor for inhibiting a tumor cell invasion or a drug for preventing and/or treating a tumor.

The active ingredient of the drug or the inhibitor provided by the present invention is any of the above antibody and/or any of the encoding genes.

Particularly, with regard to the above drug or inhibitor, the tumor may be a colon cancer; and the tumor cell may be a SW480 cell.

Use of the above antibody and/or any of the encoding genes in preparing an inhibitor for inhibiting the signal transduction pathway of the epidemic growth factor receptor also belongs to the protection scope of the present invention.

Use of the above antibody and/or any of the encoding genes in preparing an inhibitor for inhibiting a tumor cell invasion also belongs to the protection scope of the present invention.

Use of the above antibody and/or any of the encoding genes in preparing a drug for preventing and/or treating a tumor also belongs to the protection scope of the present invention.

Use of the above antibody and/or any of the encoding genes in inhibiting the signal transduction pathway of the epidemic growth factor receptor also belongs to the protection scope of the present invention.

Use of the above antibody and/or any of the encoding genes in inhibiting a tumor cell invasion also belongs to the protection scope of the present invention.

Use of the above antibody and/or any of the encoding genes in preventing and/or treating a tumor also belongs to the protection scope of the present invention.

Particularly, in the above uses, the tumor may be a colon cancer; and the tumor cell may be a SW480 cell.

Based on the establishment of the antibody-antigen crystal structure, and by means of computer simulation, the present invention subjected the surface gene from the murine variable region FR of the cetuximab antibody to mutation, making it to be similar with the human antibody FR in form, thereby obtaining an anti-EGFR humanized antibody with significantly improved affinity comparing with that of the cetuximab. The experimental results demonstrate that the antibody of the present invention has a good binding activity (with an affinity of $5.09 \times 10^{-10}$ mol/L) and an ability of inhibiting tumor cell growth and migration; however, the anti-EGFR human-murine chimeric antibody, cetuximab, commonly found in foreign market has an affinity of $1.1 \times 10^{-9}$ M. The humanized antibody of the present invention is capable of better binding with EGFR, thus guaranteeing the anti-tumor effect thereof. The present method for preparing an antiboy enables the light chain and the heavy chain to be expressed simultaneously, such that the expression ratio of the light chain to the heavy chain gets closer to 1:1, producing a higher ratio of matching double strand antibodies. In summary, the antibody and preparation method thereof of the present invention will have a broad application prospect in the field in preventing and/or treating a tumor.

BEST MODE FOR CARRYING OUT THE INVENTION

The experimental methods used in the following Examples each is a conventional method unless on therewise indicated.

The materials, reagents and the like used in the following Examples each is commercially available unless on therewise indicated.

Example 1

Obtaining of the Encoding Genes for the Light Chain and the Heavy Chain Variable Region of the Antibody Based on computer simulation, and with the amino acid sequence of the murine-human chimeric antibody, cetuximab, as a template, the surface gene of the murine FR was subjected to humanized remodeling, such that the amino acid sequence of the light chain L3 and the amino acid sequence of the heavy chain variable region H1 were designed and synthesized;

The light chain L1: the amino acid sequence is set forth by SEQ ID NO. 1 in the sequence listing; the sequence of the encoding gene is set forth by SEQ ID NO. 4 in the sequence listing;

The light chain L3: the amino acid sequence is set forth by SEQ ID NO. 2 in the sequence listing; the sequence of the encoding gene is set forth by SEQ ID NO. 5 in the sequence listing;

The heavy chain variable region H1: the amino acid sequence is set forth by SEQ ID NO. 3 in the sequence listing; the sequence of the encoding gene is set forth by SEQ ID NO. 6 in the sequence listing;

The antibody of the present invention, referred to as C5, is composed of the light chain L3 and the heavy chain variable region H1.

The encoding gene of the light chain L1 and the encoding gene of the heavy chain variable region H2 were produced by artificial synthesization.

Figure 1:
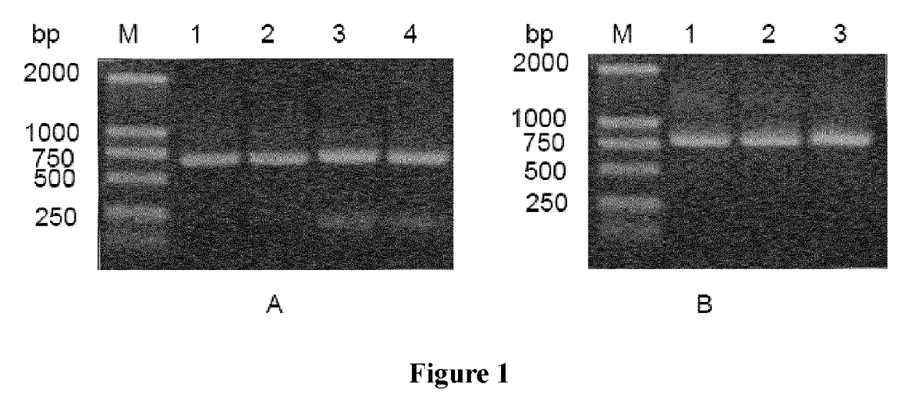
FIG. 1, an agarose gel electrophoresis of the PCR amplification products of the light chain gene and the heavy chain variable region gene.

The encoding gene of the light chain L3: an overlap PCR method was performed, wherein the encoding gene of the light chain L1 was used as a template to perform amplification with primers 1, 2, 5 and 6 so as to give the encoding gene of the light chain L3;

Primers:

(SEQ ID NO. 7)
1: 5'-gtggctagcgccgccaccatggacat-3' (NheI);

(SEQ ID NO. 8)
2: 5'-gaattcctaacactctcccctgttga-3' (EcoRI);

(SEQ ID NO. 9)
5: 5'-gctgctaatgccctgacttgcccggcaggcaatgttga-3';

(SEQ ID NO. 10)
6: 5'-gcctgccgggcaagtcagggcattagcagcaacttacactggtatcagcagaaacca-3';

Each of the amplified genes was detected by gel electrophoresis, and the result was consistent with the expected size, L and H has a fragment size of about 735 bp and 770 bp, respectively (FIG. 1). M: relative molecular mass standard; A: lane 1, light chain gene product L1, lane 3, light chain gene product L3; B: lane 1, heavy chain variable region gene product H1.

The encoding gene of the light chain L3 and the encoding gene of the heavy chain variable region H1 were separately cloned into the pMD18-T vector (recorded as the recombinant vectors pMD18-T/L3 and pMD18-T/H1, respectively), transformed into *Escherichia coli* DH5α, and then, clones were picked and, from which plasmids were extracted and identified by sequencing. The results indicated that each of the obtained gene sequences is correct.

Example 2

Preparation of the Antibody

I. Construction of the Recombinant Expression Vector:

The pIRES dual expression vector, Cat. No.: 631605, was purchased from Clontech company; the pMD18-T expression vector, Cat. No.: D504 CA, was purchased from Takara Bio Company. The pIRES vector itself contains a heavy chain constant region gene. The heavy chain constant region has an amino acid sequence as set forth by SEQ ID NO. 11 in the sequence listing, the encoding gene thereof has a genomic DNA sequence as set forth by SEQ ID NO. 12 in the sequence listing and a cDNA sequence as set forth by SEQ ID NO. 13 in the sequence listing. The heavy chain constant region gene in the pIRES vector is the genomic gene as set forth by SEQ ID NO. 12.

Figure 2:
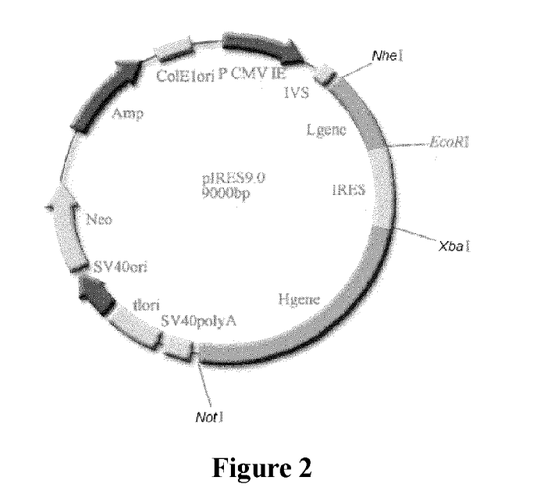
FIG. 2, a structural schematic view of an expression vector containing the antibody of the present invention.

The recombinant vector pMD18-T/L3 and pIRES dual expression vector were separately cleaved with corresponding restriction endonucleases (NheI and EcoRI), and then, the target fragments were recovered and purified after gel electrophoresis;

the light chain gene fragments L3 and the vector fragments were uniformly mixed, reacting at 16° C. for 12 h under action of the ligation agent. The reaction products were transformed into *E. coli* DH5α, and then, clones were picked and, from which plasmids were extracted and identified by sequencing. The results showed that both the insertion direction and the insertion sequence of the gene are correct in the recombinant expression vector, recorded as the recombinant expression vector pIRES/L3.

pIRES/L3 was used as a template and cleaved enzymatically with Xba I and Not I, and then, the resulting large fragments were recovered and recorded as fragment 1; pMD18-T/H1, cloned with the heavy chain variable region gene, was used as a template and cleaved enzymatically with Xba I and BamH I, and then, the heavy chain variable region fragments were recovered and recorded as fragment 2; pIRES vector, cloned with the heavy chain constant region gene, was used as a template and cleaved enzymatically with BamH I and Not I, and then, the heavy chain constant region fragments (the heavy chain constant region fragment resulting from cleavage with BamH I and Not I has a sequence as set forth by SEQ ID NO. 12) were recovered and recorded as fragment 3; fragments 1, 2 and 3 were linked to give a recombinant vector, which was then transformed into *E. coli* DH5α, after which clones were picked and, from which plasmids were extracted and identified by sequencing. The results show that structure of the resulting recombinant expression vector is correct, and the genes were inserted in correct direction and order; the light chain gene and heavy chain gene of the antibody share a common promoter; an expression plasmid was finally constructed through ligation by IRES sequence. The recombinant expression vector was recorded as pIRES/L3/H1 (FIG. 2).

II. Cell Transformation and Protein Expression 293T cell (293T human embryonic kidney T cell), Cat. No.: CRL-11268, was purchased from American Type Culture Collection (ATCC); Lipofectamine 2000, Cat. No.: 12566014, was purchased from Invitrogen company; HyQSFM4CHO medium, Cat. No.: SH30518.02, was purchased from HyClone company; rProtein A chromatography column, Cat. No.: 17-5079-01, was purchased from GE company.

293T cell was inoculated into a 10 cm-diameter petri dish at $1 \times 10^6$/ml, and cultured in a DMEM medium containing 10% fetal bovine serum at a 5% $CO_2$ incubator at 37° C. 5 µg of the resulting plasmid pIRES/L3/H1 obtained in step I was used to transfect 293T cell to give a recombinant cell 293T-pIRES/L3/H1, which was performed in accordance with the reagent instruction of Lipofectamine 2000.

The recombinant cell 293T-pIRES/L3/H1 was cultivated in a serum-free DMEM medium for 6~8 h prior to sucking out the serum-free medium and replacing with a HyQSFM4CHO medium. Then, co-cultivation continued to be conducted under the same condition for 84 h, and cell supernatant was collected at an interval of 12 h and primarily detected with the ELISA method for the expression of the antibody. Scaling-up the transfection system, cell cultivation supernatant of 4.5 L was collected and adjusted to pH 6.0~7.0 and filtered through a 0.45 µm filter film, and the antibody was then purified by the rProtein A chromatography column, which was performed in accordance with the product instruction.

The ELISA method:

1. Coating: 0.05M PH 9.0 carbonate coating buffer was used to dilute the antibody (primary antibody: goat anti-human IgG) to a protein content of 1~10 µg/ml. 0.1 ml was added into each reaction well of the polystyrene plate, staying overnight at 4°. The next day, solutions were discarded form the wells, which were washed three times with a washing buffer, each for three minutes. (Hereinafter, referred to as washing).

2. Sample loading: 0.1 ml diluted sample to be assayed was added into the above coated reaction well, incubated at 37° for 1 h, and then washed. (The blank well, positive control well and negative control well were set at the same time).

3. Loading of the enzyme-labelled antibody (secondary antibody: goat anti-human IgG-HRP (goat anti-human IgG-horseradish peroxidase)): into each reaction well, 0.1 ml freshly diluted enzyme-labelled antibody (dilution after titration) was added, incubated at 37° for 0.5~1 h, and then washed.

4. Addition of substrate for color development: into each reaction well, 0.1 ml temporarily formulated TMB substrate solution was added, staying at 37° C. for 10~30 min.

5. Termination reaction: into each reaction well, 0.05 ml 2M sulfuric acid was added.

6. Result determination: direct observations may be made on a white background with naked eyes: the darker in the reaction well, the stronger the positive degree, and the negative reaction was colorless or very light, which were denoted by "+" and "−" depending on the depth of the color displayed. The OD value also can be measured: the OD value of each well was measured, after the blank control well was set to zero, on a ELISA detector at 450 nm (if ABTS is used for color development, then at 410 nm), which, if 2.1 times greater than the prescribed OD value of the negative control, indicates a positive.

The reagents (1) Coating buffer (PH 9.6 0.05M carbonate buffer): $Na_2CO_3$ 1.59 g, $NaHCO_3$ 2.93 g, and distilled water added to 1000 ml.

(2) Washing buffer (PH 7.4 PBS): 0.15M: $KH_2PO_4$ 0.2 g, $Na_2HPO_4.12H_2O$ 2.9 g, NaCl 8.0 g, KCl 0.2 g, Tween-20 0.05% 0.5 ml, and distilled water added to 1000 ml.

(3) Dilution solution: bovine serum albumin (BSA) 0.1 g and washing buffer to 100 ml; or formulated with serums, such as sheep serum, rabbit serum and the like and the washing buffer into 5~10% for use.

(4) Stopping Solution (2M $H_2SO_4$): distilled water 178.3 ml, and concentrated sulfuric acid (98%) 21.7 ml dropwise added.

Purification of the antibody with the rProtein A chromatography column: purification medium: HiTrap rProtein A FF, 5 ml, Cat. No.: 17-5079-01, purchased from GE Company, referring to the Manual provided by the company for detailed instruction for use.

Sodium phosphate buffer (binding buffer): used as the binding buffer for Protein A purification. The formulation method was as follows: 1M $Na_2HPO_4$, 57.7 ml, and 1M $NaH_2PO_4$, 42.3 ml, were uniformly mixed to give 100 ml of 0.1M sodium phosphate buffer, pH 7.0, which was then diluted to 20 Mm with distilled water for use.

Citric acid/sodium citrate buffer (elution buffer): used as the elution buffer for Protein A purification. The formulation method was as follows: 0.1M citric acid, 186 ml, and 0.1M sodium citrate, 14 ml, were uniformly mixed to give 200 ml of 0.1M citrate buffer, pH 3.0.

Operations:

1) Cleaning up: 1M NaOH and $ddH_2O$ were sequentially used to clean the conduit, and the small filter was boiled with 0.1M NaOH for 10 min and then immersed with $ddH_2O$ for 1~2 min;

2) Setting Program and linking the rProtein A affinity chromatography column;

3) 20 mM binding buffer (pH 7.0) was used to balance the chromatography column;

4) The prepared cell supernatant was loaded at a flow rate of 1~2 ml/min; preparation of the cell supernatant: centrifugating at 12000 g for 15 min, and removing the supernatant which was then sterilized by filtering through a 0.22 um nitrocellulose filter film.

5) 1M elution buffer (pH 3.0) was used to elute the target protein when the loading was nearing completion;

6) The protein was collected, adjusted to pH 7.0 with Trise base (pH 9.0), and detected by electrophoresis;

7) The conduit and small filter were cleaned in accordance with step 1).

III. Detection of Protein

The goat anti-human IgG-HRP antibody, Cat. No.: (046K4801), was purchased from Sigma Company; the goat anti-mouse IgG1, Cat. No.: (1010-05), was purchased from SBA (Southern Biotechnology Associates, Inc.);

SDS-PAGE: 15 µl elution buffer (i.e., antibody solution) was subjected to a reducing SDS-PAGE electrophoresis on 12% gel, and stained with Coomassie brilliant blue R-250.

Figure 3:
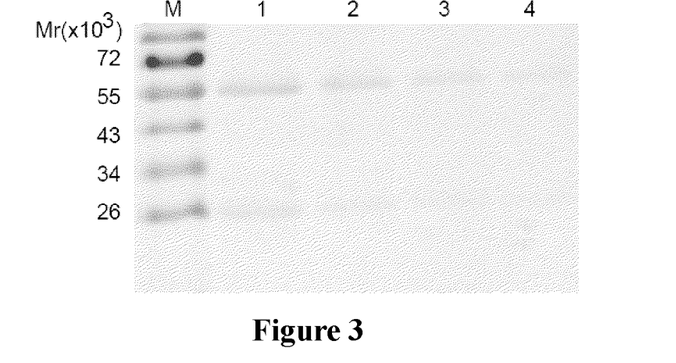
FIG. 3, a reduced SDS-PAGE assay of the antibody of the present invention.

The results indicate that the heavy chain and the light chain of the purified antibody have a relative molecular mass of $25 \times 10^3$ and $50 \times 10^3$, respectively (FIG. 3 and FIG. 4), which is consistent with the expected results. In FIG. 3, lane 4 denotes the present antibody C5, and lane 3 denotes the control, i.e., the cetuximab.

Figure 4:
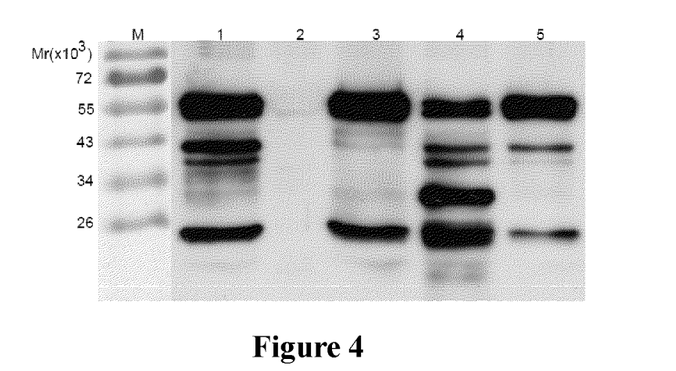
FIG. 4, an immunobiological imprinting analysis of the antibody of the present invention.

Immunobiological imprinting analysis: additional elution buffer was taken to perform the reducing SDS-PAGE electrophoresis on a 12% gel, and then transferred to a nitrocellulose membrane, which was sealed at room temperature with a membrane blocking solution (1×PBST, comprising 5% skim milk powder) for 2 h, incubated with a goat anti-human IgG-HRP antibody diluted 1:5000 for 2 h (room temperature), and then washed 3 times with 1×PBST. Finally, color was developed by using ECL, and exposures were made with X-ray film. This analysis was simultaneously performed on the control added with an anti-murine IgG1. In FIG. 4, lane 5 denotes the present antibody C5; lane 2 denotes the murine monoclonal antibody negative control; and lane 4 denotes the positive control, i.e., the cetuximab.

The immunobiological imprinting (12%) analysis demonstrates that the antibody may specifically bind a goat anti-human IgG. However, there are some non-specific hybridizing bands (including commercial cetuximab) which partially react with the anti-human IgG secondary antibody, possibly due to the mixture with a portion of non full-length heavy chain fragments during purification. Nevertheless, the above results have no influence on the affinity estimate of the antibodies. The above antibodies each does not react with the anti-murine IgG1 antibody.

Since the light chain and heavy chain of the present antibody are proportionately expressed on the same expression vector, they spontaneously constitute a complete antibody comprising two light chains and two heavy chains.

Example 3

Function Detection of the Antibody

EGFR protein was purchased from (Sigma), Cat. No.: (E2645-500UN).

I. Biacore Assay of Binding Capability Between the Antibody and Antigen

The affinity between antibody C5 and EGFR was determined with a Biacore3000 equipment. 10 mmol/L NaAc with different pH values (4.0, 4.5, 5.0 and 5.5) were formulated to dilute the EGFR protein, and after preconcentration on a CM5 chip, NaAc with optimum pH value was selected to dilute the protein. The purified antibody (i.e., the elution buffer resulting from Step II in Example 2) was covalently coupled to a CM5 sensing chip, mobile phase: HBS-EP (pH 7.4), flow rate: 20 μl/min. Five different concentrations of antibody C5 (0, 10.55, 21.1, 42.2 and 84.4 nmol/L) were taken for the detection of binding affinity with the EGFR protein. The affinity was caculated with an attached software of Biacore300. Meanwhile, the cetuximab was used as a control.

The experiments were conducted in triplicate with the average value taken as the result.

The results show that C5 displays a favorable binding activity (with an affinity of $5.09 \times 10^{-10}$ mol/L) to the antigen EGFR. The cetuximab has an affinity of $1.1 \times 10^{-9}$ M.

II. Tumor Cell Invasion Experiment

The SW480 cell, Cat. No.: (ATCC® Number: CCL-228™), was purchased from the American Type Culture Collection (ATCC); the cetuximab antibody was purchased from Merck KGaA in Germany (original English brand name: ERBITUX; original English drug name: Cetuximab; Chinese translated reference product name: aibituo ( 爱必妥 ); molecular structure name: cetuximab; country of origin: Germany; manufacturer: Merck KGaA in Germany).

The SW480 cell was cultivated with a RPMI1640 medium (purchased from Invitrogen Company, Cat. No.: 31800-022). The invasion chamber was hydrated with the serum-free RPMI1640 medium, incubating for 2 h (37°, 5% $CO_2$). The serum-free RPMI1640 was removed, and into the pore chamber of the invasion chamber (BD BioCoat™ Matrigel™ Invasion Chamber, purchased from BD Company, Cat. No.: 354480), 750 μl RPMI 1640 (containing 10% serum) was added; 475 μl RPMI1640 (containing 1% serum) was added into the insert chamber, into which, 25 μl of digested SW480 cell (cell number>$10^5$/500 μl) was added afterwards, and finally, the negative control PBS and the present antibody respectively; each sample has two pores, and the antibody has a final concentration of 100 ng/ml. After a 24 h incubation, cells that can not penetrate the basic film of the envision cassette were wiped off with a sterile cotton swab; cells penetrated the basic film were fixed, stained, and dried at room temperature prior to count under the optical microscope.

The corresponding cell number was counted under a 100× microscope for the samples in each insert chamber. Comparing the antibody group and the PBS group by using a Dunnett t3 (bilateral analysis) assay, if $P<0.05$, the differences between these two treatment effects may be considered to be statistically significant.

A variance analysis of single factor of four levels was conducted on the cell invasion experimental data by using the SPSS12.0 statistical software, which shows $F_{0.05(3,44)}=2.82$ and $P<0.05$, indicating that the cell numbers are not equal or not completely equal.

The results of Dunnett t3 (bilateral analysis, hereafter referred to as t) assay (Table 1) demonstrate that the t value of PBS group and C5 group is 1.16, and P is greater than 0.05, indicating that the anti EGFR antibody C5 has certain inhibittion to the invision of SW480 tumor cell, which, however, does not differ significantly from the control group.

TABLE 1 the results of Dunnett's t3 assay for the cell invision experiment

| Groups | n | average number of cells |
|---|---|---|
| PBS group | 12 | 86 ± 16.222 |
| C5 group | 12 | 76 ± 21.2778*** |

Note:
comparing with the PBS group,
***P = 0.928,
***t = 1.16.

INDUSTRIAL APPLICATION

The antibody of the present invention has a good binding activity (with an affinity of $5.09 \times 10^{-10}$ mol/L) and an ability of inhibiting tumor cell growth and migration; however, the anti-EGFR human-murine chimeric antibody, cetuximab, commonly found in foreign market has an affinity of $1.1 \times 10^{-9}$ M. The present humanized antibody is capable of better binding with EGFR, thus guaranteeing the anti-tumor effect thereof. The present method for preparing an antiboy enables the light chain and the heavy chain to be expressed simultaneously, such that the expression ratio of the light chain to the heavy chain gets closer to 1:1, producing a higher ratio of matching double strand antibodies. In summary, the antibody and preparation method thereof of the present invention will have a broad application prospect in the field in preventing and/or treating a tumor.

What is claimed is:

1. An antibody, wherein the heavy chain variable region of the antibody has the amino acid sequence as set forth by SEQ ID NO: 3, and the light chain of the antibody has the amino acid sequence as set forth by SEQ ID NO: 2.

2. The antibody according to claim 1, wherein the antibody comprises a heavy chain and the light chain, and the heavy chain comprises the heavy chain variable region and a heavy chain constant region.

3. The antibody according to claim 2, wherein the heavy chain constant region comprises an amino acid sequence as set forth by SEQ ID NO: 11.

4. An inhibitor for inhibiting signal transduction pathway of the epidermal growth factor receptor or a tumor cell invasion, wherein the active ingredient of the inhibitor is the antibody of claim 1.

5. The inhibitor according to claim 4, wherein the tumor is a colon cancer.

6. The inhibitor according to claim 5, wherein the tumor cell is a SW480 cell.

7. A drug for treating a tumor, wherein the active ingredient of the drug is the antibody of claim 1.

8. The drug according claim 7, wherein the tumor is a colon cancer.

9. The drug according claim 8, wherein the tumor cell is a SW480 cell.

10. A method for treating a tumor comprising administering a therapeutically effective amount of preparing a drug comprising the antibody of claim 1.

11. The method according to claim 10, wherein the tumor is a colon cancer.

12. The method according to claim 11, wherein the tumor cell is a SW480 cell.

13. A method of inhibiting signal transduction pathway of epidermal growth factor receptor comprising administering a therapeutically effective amount of the antibody of claim 1 to an individual in need thereof.

14. A method of inhibiting a tumor cell invasion comprising administering a therapeutically effective amount of the antibody of claim 1 to an individual in need thereof.

15. The method according to claim 14, wherein the tumor is a colon cancer.

16. A method of treating a tumor comprising administering a therapeutically effective amount of the antibody of claim 1 to an individual in need thereof.

17. The method according to claim 16, wherein the tumor is a colon cancer.

18. The method according to claim 15, wherein the tumor cell is a SW480 cell.

19. The method according to claim 17, wherein the tumor cell is a SW480 cell.

* * * * *

UNITED STATES PATENT AND TRADEMARK OFFICE
CERTIFICATE OF CORRECTION

PATENT NO. : 8,486,895 B2
APPLICATION NO. : 13/509237
DATED : July 16, 2013
INVENTOR(S) : David Weaver et al.

It is certified that error appears in the above-identified patent and that said Letters Patent is hereby corrected as shown below:

In the Specification,
At Column 3, line 67, change "5.09×10-1°" to --5.09×10-10--.
At Column 4, line 6, change "antiboy" to --antibody--.
At Column 4, line 32, change "on therewise" to --otherwise--.
At Column 4, line 34, change "on therewise" to --otherwise--.
At Column 5, line 57-65, Delete "the light chain gene fragments L3 and..........................recombinant expression vector pIRES/L3." and insert the same on Col. 5, line 56, as the continuation of the same Paragraph.
At Column 7, line 1, change "4°." to --4° C.--.
At Column 7, line 6, change "37°" to --37° C.--.
At Column 7, line 13, change "37°" to --37° C.--.
At Column 9, line 9, change "caculated" to --calculated--.
At Column 9, line 9-10, change "Biacore300." to --Biacore3000.--.
At Column 9, line 28, change "(37°," to --(37° C.,--.
At Column 10, line 13-14, change "inhibittion" to --inhibition--.
At Column 10, line 38, change "antiboy" to --antibody--.

In the Sequence Listing,
At Column 9-10, line 5, change "artifical" to --artificial--.
At Column 11-12, line 26, change "artifical" to --artificial--.
At Column 13-14, line 8, change "artifical" to --artificial--.
At Column 13-14, line 40, change "artifical" to --artificial--.
At Column 15-16, line 10, change "artifical" to --artificial--.
At Column 15-16, line 28, change "artifical" to --artificial--.
At Column 17-18, line 5, change "artifical" to --artificial--.
At Column 17-18, line 13, change "artifical" to --artificial--.
At Column 17-18, line 21, change "artifical" to --artificial--.
At Column 17-18, line 29, change "artifical" to --artificial--.
At Column 17-18, line 37, change "artifical" to --artificial--.

Signed and Sealed this
Twenty-fourth Day of February, 2015

Michelle K. Lee
*Deputy Director of the United States Patent and Trademark Office*

At Column 19-20, line 34, change "artifical" to --artificial--
At Column 21-22, line 21, change "artifical" to --artificial--.

In the Claims,
At Column 23, line 23, change "according" to --according to--.
At Column 23, line 25, change "according" to --according to--.

SEQUENCE LISTING

<160> NUMBER OF SEQ ID NOS: 13

<210> SEQ ID NO 1
<211> LENGTH: 214
<212> TYPE: PRT
<213> ORGANISM: artifical sequence
<220> FEATURE:
<223> OTHER INFORMATION: Chemically synthesized

<400> SEQUENCE: 1

Glu Leu Val Met Thr Gln Ser Pro Ser Ser Leu Ser Ala Ser Val Gly
1               5                   10                  15

Asp Arg Val Asn Ile Ala Cys Arg Ala Ser Gln Ser Ile Glu Thr Asn
            20                  25                  30

Leu His Trp Tyr Gln Gln Lys Pro Gly Lys Ala Pro Arg Leu Leu Ile
        35                  40                  45

```
Lys Tyr Thr Ser Arg Leu His Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Ile Tyr Tyr Cys Gln Gln Asn Asn Asn Trp Pro Thr
                 85                  90                  95

Thr Phe Gly Gly Gly Thr Lys Val Glu Ile Lys Arg Thr Val Ala Ala
             100                 105                 110

Pro Ser Val Phe Ile Phe Pro Pro Ser Asp Glu Gln Leu Lys Ser Gly
         115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 2
<211> LENGTH: 214
<212> TYPE: PRT
<213> ORGANISM: artifical sequence
<220> FEATURE:
<223> OTHER INFORMATION: Chemically synthesized

<400> SEQUENCE: 2

Glu Leu Val Met Thr Gln Ser Pro Ser Ser Leu Ser Ala Ser Val Gly
 1               5                  10                  15

Asp Arg Val Asn Ile Ala Cys Arg Ala Ser Gln Gly Ile Ser Ser Asn
                 20                  25                  30

Leu His Trp Tyr Gln Gln Lys Pro Gly Lys Ala Pro Arg Leu Leu Ile
             35                  40                  45

Lys Tyr Thr Ser Arg Leu His Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Ile Tyr Tyr Cys Gln Gln Asn Asn Asn Trp Pro Thr
                 85                  90                  95

Thr Phe Gly Gly Gly Thr Lys Val Glu Ile Lys Arg Thr Val Ala Ala
             100                 105                 110

Pro Ser Val Phe Ile Phe Pro Pro Ser Asp Glu Gln Leu Lys Ser Gly
         115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

Ala Cys Glu Val Thr His Gln Gly Leu Ser Ser Pro Val Thr Lys Ser
        195                 200                 205

Phe Asn Arg Gly Glu Cys
    210

<210> SEQ ID NO 3
<211> LENGTH: 223
<212> TYPE: PRT
<213> ORGANISM: artifical sequence
<220> FEATURE:
<223> OTHER INFORMATION: Chemically synthesized

<400> SEQUENCE: 3

Gln Val Lys Leu Leu Glu Gln Ser Gly Ala Glu Val Lys Lys Pro Gly
1               5                   10                  15

Ala Ser Val Lys Val Ser Cys Lys Ala Ser Gly Phe Ser Ile Gly Asn
            20                  25                  30

Tyr Gly Ile His Trp Val Arg Gln Ala Pro Gly Gln Arg Leu Glu Trp
        35                  40                  45

Met Gly Gly Ile Trp Ser Gly Gly Asn Ala Asp Tyr Ala Gln Lys Phe
    50                  55                  60

Gln Gly Arg Val Thr Ile Thr Arg Asp Thr Ser Ala Thr Thr Ala Tyr
65                  70                  75                  80

Met Gly Leu Ser Ser Leu Arg Pro Glu Asp Thr Ala Val Tyr Tyr Cys
                85                  90                  95

Ala Arg Val Gly Thr Tyr Tyr Asp Tyr Glu Phe Asp Val Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Val Glu Pro Lys Ser Cys
    210                 215                 220

<210> SEQ ID NO 4
<211> LENGTH: 645
<212> TYPE: DNA
<213> ORGANISM: artifical sequence
<220> FEATURE:
<223> OTHER INFORMATION: Chemically synthesized

<400> SEQUENCE: 4
gaactcgtca tgacccagtc tccatcctcc ctgtctgcat ctgtaggaga cagagtcaac      60
attgcctgcc gggcaagtca gagcattgaa actaacttac actggtatca gcagaaacca     120
gggaaagccc ctagactcct gatcaaatat acctccagat acatagtgg ggtcccatca      180 agattcagcg gcagtggatc tgcacagat tcactctca ccatcagcag cctgcagcct       240
gaagattttg caatctatta ctgtcagcaa aataacaatt ggcctactac gttcggcgga     300

```
gggaccaagg tggaaatcaa acgaactgtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg ataacgccc tccaatcggg taactcccag     480
gagagtgtca cagagcagga cagcaaggac agcacctaca gcctcagcag cacccctgacg   540 ctgagcaaag cagactacga gaaacacaaa gtctacgcct gcgaagtcac ccatcagggc    600
ctgagctcgc ccgtcacaaa gagcttcaac aggggagagt gttag                    645

<210> SEQ ID NO 5
<211> LENGTH: 642
<212> TYPE: DNA
<213> ORGANISM: artifical sequence
<220> FEATURE:
<223> OTHER INFORMATION: Chemically synthesized

<400> SEQUENCE: 5
gaactcgtca tgacccagtc tccatcctcc ctgtctgcat ctgtaggaga cagagtcaac     60
attgcctgcc gggcaagtca gggcattagc agcaacttac actggtatca gcagaaacca    120
gggaaagccc ctagactcct gatcaaatat acctccagat tacatagtgg ggtcccatca    180
agattcagcg gcagtggatc tggcacagat ttcactctca ccatcagcag cctgcagcct    240
gaagattttg caatctatta ctgtcagcaa aataacaatt ggcctactac gttcggcgga    300
gggaccaagg tggaaatcaa acgaactgtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg ataacgccc tccaatcggg taactcccag     480
gagagtgtca cagagcagga cagcaaggac agcacctaca gcctcagcag cacccctgacg   540 ctgagcaaag cagactacga gaaacacaaa gtctacgcct gcgaagtcac ccatcagggc    600
ctgagctcgc ccgtcacaaa gagcttcaac aggggagagt gt                       642

<210> SEQ ID NO 6
<211> LENGTH: 669
<212> TYPE: DNA
<213> ORGANISM: artifical sequence
<220> FEATURE:
<223> OTHER INFORMATION: Chemically synthesized

<400> SEQUENCE: 6
caggtgaagc tgctggagca gtctggggct gaagtgaaga agcctggggc ctcagtgaag     60
gtttcctgca aggcatctgg attcagcatc ggcaactacg gcatccactg ggtgcgacag    120
gcccctggac aaagacttga gtggatggga ggaatctgga gtggtggtaa cgccgactac    180
gcacagaaat tccagggcag agtcaccatc accagggaca cgtccgctac tacagcctac    240
atgggcctgt ctagcctgag acccgaggac acggccgtat attactgtgc gagagtgggc    300
acttattacg actacgagtt cgacgtgtgg ggccagggaa ccctggtcac cgtctcctca    360
gcctccacca agggcccatc ggtcttcccc ctggcaccct cctccaagag cacctctggg    420
ggcacagcgg ccctgggctg cctggtcaag gactacttcc ccgaaccggt gacggtgtcg    480
tggaactcag gcgccctgac cagcggcgtg cacaccttcc cggctgtcct acagtcctca    540
ggactctact ccctcagcag cgtggtgacc gtgccctcca gcagcttggg cacccagacc    600
tacatctgca acgtgaatca caagcccagc aacaccaagg tggacaagaa agttgagccc    660
```

-continued aaatcttgt                                                                  669

<210> SEQ ID NO 7
<211> LENGTH: 26
<212> TYPE: DNA
<213> ORGANISM: artifical sequence
<220> FEATURE:
<223> OTHER INFORMATION: Chemically synthesized

<400> SEQUENCE: 7
gtggctagcg ccgccaccat ggacat                                                26

<210> SEQ ID NO 8
<211> LENGTH: 26
<212> TYPE: DNA
<213> ORGANISM: artifical sequence
<220> FEATURE:
<223> OTHER INFORMATION: Chemically synthesized

<400> SEQUENCE: 8
gaattcctaa cactctcccc tgttga                                                26

<210> SEQ ID NO 9
<211> LENGTH: 38
<212> TYPE: DNA
<213> ORGANISM: artifical sequence
<220> FEATURE:
<223> OTHER INFORMATION: Chemically synthesized

<400> SEQUENCE: 9
gctgctaatg ccctgacttg cccggcaggc aatgttga                                   38

<210> SEQ ID NO 10
<211> LENGTH: 57
<212> TYPE: DNA
<213> ORGANISM: artifical sequence
<220> FEATURE:
<223> OTHER INFORMATION: Chemically synthesized

<400> SEQUENCE: 10
gcctgccggg caagtcaggg cattagcagc aacttacact ggtatcagca gaaacca             57

<210> SEQ ID NO 11
<211> LENGTH: 330
<212> TYPE: PRT
<213> ORGANISM: artifical sequence
<220> FEATURE:
<223> OTHER INFORMATION: Chemically synthesized

<400> SEQUENCE: 11

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

-continued

```
Lys Ala Glu Pro Lys Ser Cys Asp Lys Thr His Thr Cys Pro Pro Cys
                100                 105                 110
Pro Ala Pro Glu Leu Leu Gly Gly Pro Ser Val Phe Leu Phe Pro Pro
            115                 120                 125
Lys Pro Lys Asp Thr Leu Met Ile Ser Arg Thr Pro Glu Val Thr Cys
130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Ala Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 12
<211> LENGTH: 1795
<212> TYPE: DNA
<213> ORGANISM: artifical sequence
<220> FEATURE:
<223> OTHER INFORMATION: Chemically synthesized

<400> SEQUENCE: 12
gctagcacca agggcccatc ggtcttcccc ctggcaccct cctccaagag cacctctggg      60
ggcacagcgg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgaca gtgccctcca gcagcttggg cacccagacc     240
tacatctgca acgtgaatca caagcccagc aacaccaagg tggacaagaa agcaacaggt     300
aagtggatcc ggagggaggg tgtctgctgg aagcaggctc agcgctcctg cctggacgca     360
tcccggctat gcagccccag tccagggcag caaggcaggc ccgtctgcct cttcacccg      420 gaggcctctg cccgccccac tcatgctcag ggagagggtc ttctggcttt ttccccaggc     480
tctgggcagg cacaggctag gtgcccctaa cccaggccct gcacacaaag ggcaggtgc      540 tgggctcaga cctgccaaga gccatatccg ggaggacccc gcccctgacc taagcccacc     600
ccaaaggcca aactctccac tccctcagct cggacacctt ctctcctccc agattccagt     660
aactcccaat cttctctctg cagagcccaa atccttgtga caaaactcaca catgcccacc     720 gtgcccaggt aagccagccc aggcctcgcc ctccagctca aggcgggaca ggtgccctag     780
```

```
agtagcctgc atccagggac aggccccagc cgggtgctga cacgtccacc tccatctctt    840
cctcagcacc tgaactcctg gggggaccgt cagtcttcct cttcccccca aacccaagg    900 acaccctcat gatctcccgg acccctgagg tcacatgcgt ggtggtggac gtgagccacg    960
aagaccctga ggtcaagttc aactggtacg tggacggcgt ggaggtgcat aatgccaaga   1020
caaagccgcg ggaggagcag tacaacagca cgtaccgtgt ggtcagcgtc ctcaccgtcc   1080
tgcaccagga ctggctgaat ggcaaggagt acaagtgcaa ggtctccaac aaagccctcc   1140 cagccccat cgagaaaacc atctccaaag ccaaaggtgg acccgtggg gtgcgagggc     1200 cacatggaca gaggccggct cggcccaccc tctgccctgg gagtgaccgc tgtaccaacc   1260
tctgtcccta cagggcagcc ccgagaacca caggtgtaca ccctgccccc atcccgggat   1320
gagctgacca agaaccaggt cagcctgacc tgcctggtca aaggcttcta tcccagcgac   1380
atcgccgtgg agtgggagag caatgggcag ccggagaaca actacaaggc cacgcctccc   1440
gtgctggact ccgacggctc cttcttcctc tacagcaagc tcaccgtgga caagagcagg   1500
tggcagcagg ggaacgtctt ctcatgctcc gtgatgcatg aggctctgca caaccactac   1560
acgcagaaga gcctctccct gtctccgggt aaatgagtgc gacggccggc aagccccgc    1620 tccccgggct ctcgcggtcg cacgaggatg cttggcacgt accccgtgta catacttccc   1680
gggcgcccag catggaaata aagcacccag cgctgccctg gcccctgcg agactgtgat    1740 ggttctttcc acgggtcagg ccgagtctga ggcctgagtg catgaggga ggcag         1795

<210> SEQ ID NO 13
<211> LENGTH: 993
<212> TYPE: DNA
<213> ORGANISM: artifical sequence
<220> FEATURE:
<223> OTHER INFORMATION: Chemically synthesized

<400> SEQUENCE: 13
gctagcacca agggcccatc ggtcttcccc ctggcaccct cctccaagag cacctctggg     60
ggcacagcgg ccctgggctg cctggtcaag gactacttcc ccgaaccggt gacggtgtcg    120
tggaactcag gcgccctgac cagcggcgtg cacaccttcc cggctgtcct acagtcctca    180
ggactctact ccctcagcag cgtggtgaca gtgccctcca gcagcttggg cacccagacc    240
tacatctgca acgtgaatca caagcccagc aacaccaagg tggacaagaa agcagagccc    300
aaatcttgtg acaaaactca cacatgccca ccgtgcccag cacctgaact cctgggggga    360
ccgtcagtct tcctcttccc cccaaaaccc aaggacaccc tcatgatctc ccggacccct    420
gaggtcacat gcgtggtggt ggacgtgagc cacgaagacc ctgaggtcaa gttcaactgg    480
tacgtggacg gcgtggaggt gcataatgcc aagacaaagc cgcggaggga gcagtacaac    540
agcacgtacc gtgtggtcag cgtcctcacc gtcctgcacc aggactggct gaatggcaag    600
gagtacaagt gcaaggtctc caacaaagcc ctcccagccc ccatcgagaa aaccatctcc    660
aaagccaaag gtcagccccg agaaccacag gtgtacaccc tgcccccatc ccgggatgag    720
ctgaccaaga accaggtcag cctgacctgc ctggtcaaag gcttctatcc cagcgacatc    780
gccgtggagt gggagagcaa tgggcagccg gagaacaact acaaggccac gcctcccgtg    840
ctggactccg acggctcctt cttcctctac agcaagctca ccgtggacaa gagcaggtgg    900
cagcagggga acgtcttctc atgctccgtg atgcatgagg ctctgcacaa ccactacacg    960
cagaagagcc tctccctgtc tccgggtaaa tga                                 993
```